(12) United States Patent
Tanaka et al.

(10) Patent No.: US 7,776,936 B2
(45) Date of Patent: Aug. 17, 2010

(54) ONE-PACK TYPE DENTAL ADHESIVE COMPOSITION

(75) Inventors: Hisaki Tanaka, Kyoto (JP); Toshihide Fujii, Kyoto (JP); Yutaka Yamaguchi, Kyoto (JP); Mikito Deguchi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 59 days.

(21) Appl. No.: 12/230,225

(22) Filed: Aug. 26, 2008

(65) Prior Publication Data

US 2009/0076182 A1  Mar. 19, 2009

(30) Foreign Application Priority Data

Sep. 14, 2007 (JP) ............................... 2007-239651

(51) Int. Cl.
*A61K 6/00* (2006.01)
(52) U.S. Cl. ............................ 522/79; 522/171; 522/83; 522/168; 523/118
(58) Field of Classification Search ................. 522/168, 522/171, 79, 83; 523/115, 116, 118
See application file for complete search history.

(56) References Cited

U.S. PATENT DOCUMENTS

| | | | | |
|---|---|---|---|---|
| 4,539,382 A | * | 9/1985 | Omura et al. | 526/276 |
| 4,872,936 A | * | 10/1989 | Engelbrecht | 156/307.3 |
| 5,321,053 A | * | 6/1994 | Hino et al. | 522/26 |
| 5,530,038 A | * | 6/1996 | Yamamoto et al. | 523/116 |
| 5,670,657 A | * | 9/1997 | Kojima et al. | 549/39 |
| 5,707,611 A | * | 1/1998 | Ikemura et al. | 424/53 |
| 6,900,251 B2 | * | 5/2005 | Moszner et al. | 522/171 |
| 2010/0069524 A1 | * | 3/2010 | Tanaka et al. | 522/171 |

* cited by examiner

*Primary Examiner*—Susan W Berman
(74) *Attorney, Agent, or Firm*—Wenderoth, Lind & Ponack, L.L.P.

(57) ABSTRACT

An object of the present invention is to provide a one-pack type dental adhesive composition which can exhibit excellent adhesion to any material, for example, dental ceramics, organic composites containing inorganic compounds, dental noble metals and dental non-noble metals, and also has excellent storage stability.

Disclosed is a one-pack type dental adhesive composition comprising a silane coupling agent as a component (a), an acidic group-containing polymerizable monomer as a component (b), a sulfur atom-containing polymerizable monomer as a component (d), and other components.

2 Claims, No Drawings

ONE-PACK TYPE DENTAL ADHESIVE COMPOSITION

BACKGROUND OF THE INVENTION

1. Field of the Invention

The present invention relates to a one-pack type dental adhesive composition which can exhibit excellent adhesion to any material, for example, dental ceramics, organic composites containing inorganic compounds (hereinafter referred to as "composite materials"), noble and non-noble metals for use in dental procedures, and which also exhibits excellent storage stability.

2. Description of the Related Art

Composite materials of inorganic materials and inorganic/organic composite materials are often used as dental restorative materials. Typical examples thereof include dental porcelain (containing silicon dioxide as a main component), alumina core, zirconia core and composite. Composites are prepared by mixing an inorganic powder with a resin and the resultant mixture is in the form of a paste. Metallic materials are also used.

There have hitherto been made a trial of improving surface adhesion using silane coupling agents and a trial of improving surface adhesion using acid monomers. It is known that the silane coupling agents improve adhesion to materials having silicon dioxide as a main component. The acid monomers improve adhesion to materials having alumina or zirconia as a main component.

Among metals used in dental procedures (hereafter "dental metals"), non-noble metal alloys contain nickel, chromium, copper and titanium as main components. Japanese Examined Patent Publication (Kokoku) No. 60-42222 discloses the use of 4-acryloxylethyltrimellitate esters and acid anhydrides thereof and phosphate ester derivatives thereof so as to solve non-noble metal adhesion, however, adhesion to noble metals is insufficient. Among dental metals, noble metal alloys contain gold, platinum, palladium and silver as main components. The surface of these metals was usually subjected to tin plating or oxidation treatment in advance of bonding. However, this treatment was complicated and a sufficient adhesive force was not obtained.

Japanese Examined Patent Publication (Kokoku) No. 5-67146 reports that an adhesive force to a noble metal alloy can be improved similarly by applying a composition comprising a (meth)acrylate ester having a triazinethiol group and a volatile solvent on the surface, on which the noble metal is to be deposited, before applying an adhesive. However, adhesion to the non-noble metal alloy was found to be insufficient.

Japanese Unexamined Patent Publication (Kokai) No. 7-258248 proposes the use of a (meth)acrylate ester derivative having a disulfide cyclic group so as to solve noble metal adhesion. That is, a disulfide cyclic group-containing compound has a high adhesive force to noble metal and this technique using an adhesive composition comprising a (meth)acrylate ester derivative having a disulfide cyclic group and an organic solvent was expected to improve adhesion of an organic material to a noble metal alloy. However, the adhesive composition did not have enough adhesion to endure the severe intraoral environment and is also insufficient with respect to adhesion to a non-noble metal alloy.

Furthermore, Japanese Unexamined Patent Publication (Kokai) No. 9-67546 proposes a composition containing an acidic compound blended therein so as to enhance noble metal adhesion of the sulfur-containing triazine ring compound. Although a technique using the composition was expected to improve adhesion of an organic material to a non-noble metal and a noble metal alloy, water resistance was still insufficient. When partially damaged dental material is restored, it is sometimes unclear what kind of metal had been used. In such a case, a sufficient adhesive force may not be obtained if a proper kind of a surface treating agent (primer) is not used. For example, when a surface treating agent for a non-noble metal (primer) is used for a noble metal alloy or when a surface treating agent for a noble metal (primer) is used for a non-noble metal alloy, a sufficient adhesion cannot be obtained.

However, as described above, since silica-based, alumina-based, zirconia-based and metal-based materials are used in dental restorative materials, it was necessary to select and apply an adhesive material according to the adherend.

To solve these problems, adhesive materials containing both a silane coupling agent and an acid monomer have recently been marketed. However, since the silane coupling agent and the acid monomer cannot be stored in the same solvent for a long period, it was necessary to mix the two kinds of materials immediately before use.

There has been a need for materials which can be used regardless of the kind of adherend and which do not require a troublesome mixing operation before use.

Japanese Unexamined Patent Publication (Kokai) No. 63-51308 and Japanese Unexamined Patent Publication (Kokai) No. 7-277913 disclose dental adhesive compositions using a combination of a silane coupling agent and a phosphate ester monomer to bond a dental porcelain containing silicon dioxide with dental restorative materials such as a dental resin and a dental alloy.

However, since the silane coupling agent and the acid monomer do not readily coexist, it was necessary to mix them before use.

Japanese Unexamined Patent Publication (Kokai) No. 9-137129 discloses a dental adhesive composition comprising a coating solution containing a silane coupling agent and an acidic compound such as an organic carboxylic acid, and a coating material constituted by a polymerizable monomer which is applied on a surface on which the coating solution is to be applied, and which is polymerized in the presence of a polymerization catalyst. However, since this dental adhesive composition displays almost no adhesion to aluminum oxide or zirconium oxide, selective use with respect to the adherend was required.

Japanese Unexamined Patent Publication (Kokai) No. 2006-45179 discloses a dental adhesive composition for bonding a dental material composed of an inorganic compound or an organic composite containing an inorganic compound, and also proposes a dental adhesive composition having adhesion to aluminum oxide or zirconium oxide.

However, since a silane coupling agent is deteriorated by a phosphonic acid group-containing a (meth)acrylate-based monomer, it is difficult to stably exhibit the bonding effect for a long term. The silane coupling agent and an acid monomer do not readily and it was necessary to mix them before use.

Japanese Unexamined Patent Publication (Kokai) No. 2006-45094 describes a two-pack mixing type primer composition used for a pretreatment of the surface, on which a prosthesis made of a cured dental composite material is to be deposited, thereby improving adhesion before application of the adhesive material when the cured dental composite material is bonded with a dental material. However, this adhesive material has no adhesion to porcelain and has a primer composition which requires mixing of two liquids before bonding.

Japanese Unexamined Patent Publication (Kokai) No. 2000-248201 discloses a composition which exhibits sufficient adhesion to any of a base metal, a noble metal alloy and ceramics. However, when a silane coupling agent and an acidic group-containing polymerizable monomer are used as a one-pack type composition, serious defects with respect to storage stability of the one-pack type composition occurred.

Japanese Unexamined Patent Publication (Kokai) No. 2002-265312 discloses a technique using a composition which exhibits sufficient adhesion to any of dentin, a base metal alloy, a noble metal alloy and ceramics. However, when a silane coupling agent and an acidic group-containing polymerizable monomer are used as a one-pack type composition, serious defects with respect to storage stability of a one-pack type composition occurred.

SUMMARY OF THE INVENTION

An object of the present invention is to exhibit excellent adhesion to any material, for example, dental ceramics, organic composites containing inorganic compounds, dental noble metals and dental non-noble metals. There has been a particular need for materials which enable adhesion in a one-pack form without selecting the kind of silica-based, alumina-based, zirconia-based and metal-based materials.

Another object of the present invention is to provide a dental adhesive composition which displays excellent use characteristics and which incorporates many user requirements such as reductions in operation time and reductions in technical errors. In other words a one-pack type dental adhesive composition is provided.

In the present invention, typical examples of the dental adhesive composition include a dental primer, a dental adhesive material and a dental adhesive restorative material.

The dental adhesive composition of the present invention is a one-pack type dental adhesive composition prepared so that a silane coupling agent, an acidic group-containing polymerizable monomer and a sulfur atom-containing polymerizable monomer coexist in the same solution.

The present invention provides a one-pack type dental primer comprising a silane coupling agent as a component (a), an acidic group-containing polymerizable monomer as a component (b), a volatile organic solvent as a component (c), and a sulfur atom-containing polymerizable monomer as a component (d), wherein the content of the component (a) is from 1 to 60 parts by weight based on the entire composition and the content of the component (b) is from 1.0 to 20.0 parts by weight based on 100 parts by weight of the component (a).

The one-pack type dental primer of the present invention has an acidic group-containing polymerizable monomer as the component (b) is a phosphonic acid group-containing (meth)acrylate-based monomer represented by the following general formula [1]:

[Chemical Formula 1]

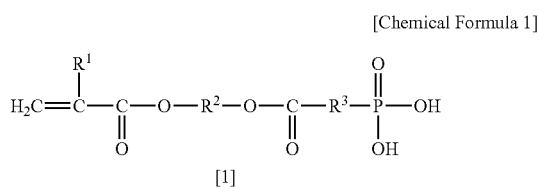

[1]

wherein $R^1$ represents a hydrogen atom or a methyl group, $R^2$ represents an optionally substituted an alkylene group having 1 to 20 carbon atoms, and $R^3$ represents an optionally substituted an alkylene group having 1 to 15 carbon atoms. The sulfur atom-containing polymerizable monomer as the component (d) is a (meth)acrylate ester derivative having a disulfide cyclic group represented by the general formula [2]:

[Chemical Formula 2]

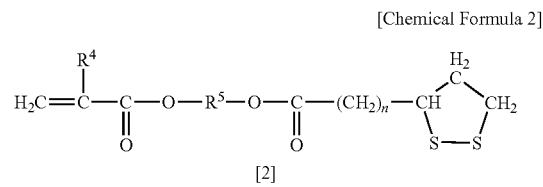

[2]

wherein $R^4$ represents a hydrogen atom or a hydrocarbon group having 1 to 3 carbon atoms, $R^5$ represents an optionally substituted alkylene group having 1 to 30 carbon atoms, and n represents an integer of 0 to 15.

The present invention also provides a one-pack type dental primer comprising a silane coupling agent as a component (a), an acidic group-containing polymerizable monomer as a component (b), a sulfur atom-containing polymerizable monomer as a component (d), a radical polymerizable monomer as a component (e), and a photopolymerization initiator as a component (f), wherein the content of the component (b) is from 1.0 to 20.0 parts by weight based on 100 parts by weight of the component (a).

The one-pack type dental primer of the present invention has an acidic group-containing polymerizable monomer as the component (b) is a phosphonic acid group-containing (meth)acrylate-based monomer represented by the following general formula [1]:

[Chemical Formula 3]

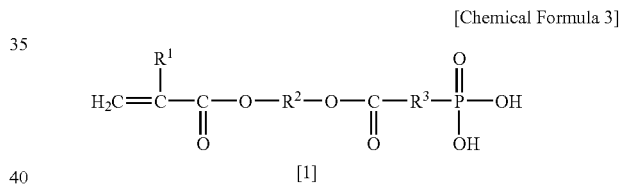

[1]

wherein $R^1$ represents a hydrogen atom or a methyl group, $R^2$ represents an optionally substituted alkylene group having 1 to 20 carbon atoms, and $R^3$ represents an optionally substituted alkylene group having 1 to 15 carbon atoms. The sulfur atom-containing polymerizable monomer as the component (d) is a (meth)acrylate ester derivative having a disulfide cyclic group represented by the general formula [2]:

[Chemical Formula 4]

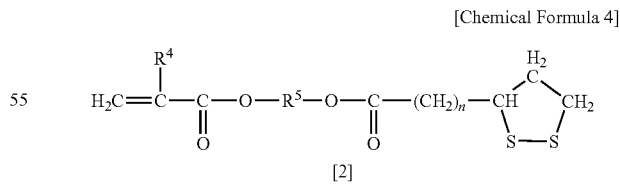

[2]

wherein $R^4$ represents a hydrogen atom or a hydrocarbon group having 1 to 3 carbon atoms, $R^5$ represents an optionally substituted alkylene group having 1 to 30 carbon atoms, and n represents an integer of 0 to 15.

The present invention further provides a one-pack type dental primer comprising a silane coupling agent as a component (a), an acidic group-containing polymerizable monomer as a component (b), a radical polymerizable monomer as a component (e), a photopolymerization initiator as a component (f), and a filler as a component (g), wherein the content of the component (b) is from 1.0 to 20.0 parts by weight based on 100 parts by weight of the component (a).

Employment of these configurations imparts excellent adhesion and durability, which have never been attained by the prior art, to dental ceramics, organic composites containing inorganic compounds, dental noble metals and dental non-noble metals, and thus resultant dental adhesive composition has simple and easy use characteristics and excellent storage stability.

The present invention has a silane coupling agent as the component (a) is represented by the following general formula [3]:

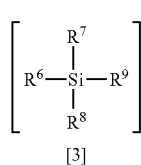

[Chemical Formula 5]

[3]

wherein $R^6$ represents an organic residue having at least one functional group selected from the group consisting of a (meth)acryloyl group, a vinyl group, a styryl group, a mercapto group and an epoxy group; $R^7$ represents a hydroxyl group, an alkyl group having 1 to 5 carbon atoms or an alkoxy group having 1 to 5 carbon atoms; and $R^8$ and $R^9$ each represents a hydroxyl group or an alkoxy group having 1 to 5 carbon atoms.

A silane coupling agent as the component (a) is preferably a compound of the general formula [3] in which $R^6$ represents an organic residue having at least one functional group selected from the group consisting of a (meth)acryloyl group and a vinyl group; $R^7$ represents a hydroxyl group, an alkyl group having 1 to 5 carbon atoms or an alkoxy group having 1 to 5 carbon atoms; and $R^8$ and $R^9$ each represents a hydroxyl group or an alkoxy group having 1 to 5 carbon atoms.

The present invention has an acidic group-containing polymerizable monomer as the component (b) is 4-(meth)acryloxyethyltrimellitic acid, 4-(meth)acryloxyethyltrimellitic anhydride, 6-(meth)acryloxyhexylphosphonoacetate, 6-(meth)acryloxyhexylphosphonopropionate, or 10-(meth)acryloxydecylhydrogen phosphate.

The present invention has a volatile organic solvent as the component (c) is methanol, ethanol, isopropanol, butanol, acetone, ethyl acetate, or isopropylether, or a radical polymerizable monomer such as (meth)acrylate ester, (meth)acrylamide or vinyl ester.

The present invention has a sulfur atom-containing polymerizable monomer as the component (d) is a (meth)acrylate ester derivative having a disulfide cyclic group.

Use of the dental adhesive composition of the present invention enables excellent adhesion and durability to any material, for example, dental ceramics, organic composites containing inorganic compounds, dental noble metals and dental non-noble metals. Furthermore, the resultant dental adhesive composition displays excellent storage stability and can be used simply and easily. Adhesion is particularly excellent to silica-based, alumina-based and zirconia-based dental materials, noble metals and inorganic/organic composite materials.

A specific example of using the dental adhesive composition of the present invention is as follows: when any one of a dental restorative component, a dental restorative material and a dental device are bonded to each other, the dental adhesive composition of the present invention is used for bonding with a resin-based material when the dental restorative component is formed from dental ceramics containing silicon dioxide as a main component, dental ceramics containing aluminum dioxide and zirconium dioxide as main components, a resin-based material containing ceramics or an inorganic filler, a noble metallic material or an non-noble metallic material.

The dental adhesive restorative material has adhesive characteristics resulting from use of a technique of the present invention with respect to a dental restorative material. Specifically, it is an adhesive composite resin for a facing crown or breakage restoration.

However, dentists can carry out a bonding operation simply and easily by using the dental adhesive composition of the present invention without selecting the adherend. Furthermore, the present invention relates to a dental adhesive composition and the method of use is almost the same as in case of various adhesive compositions which have conventionally been used. Namely, since the method of use is the same regardless of an adhesive composition having an essentially new function, the dental adhesive composition of the present invention will be easily accepted by dentists as users and thus the present invention is an invention which is useful for all dental procedures.

The dental adhesive composition in the present invention is a one-pack type adhesive composition and therefore can be simply and easily used. Since a conventional dental adhesive composition is in a two-pack mixing form, a mixing operation is required before use and the operation is complicated, leading to loss as a result of the time involved. Furthermore, it is unclear whether or not a proper mixing ratio of two liquid is ensured and a sufficient mixing operation is carried out and technical errors may occur, leading to loss.

The dental adhesive composition of the present invention can also be used as a primer and can be used in combination with other adhesive materials.

DETAILED DESCRIPTION OF THE INVENTION

Concrete embodiments of the dental adhesive composition of the present invention are dental ceramics, organic composites containing inorganic compounds, dental noble metals, one-pack type dental primers for dental non-noble metals, dental adhesive materials, and dental adhesive restorative materials. Adhesive composite resins are contained in dental adhesive restorative material, and resin cements are contained in dental adhesive materials.

Particularly, the one-pack type dental primer can exhibit high adhesion by a very simple treatment in the use as dental ceramics, organic composites containing inorganic compounds, dental noble metals, and dental non-noble metals.

Aspects of the dental adhesive composition of the present invention include excellent use as dental bonding agents as dental adhesives, orthodontic adhesive materials, resin cements and dual-cure type resin cements. As applications for dental adhesion restored materials, the dental adhesive composition can be used in opaque agents, compomers, resin cores, and adhesive composite resin facing crown materials.

The silane coupling agent as the component (a) used in the present invention is preferably a silane coupling agent having a functional group, which is copolymerizable with a polymerizable monomer component in a dental adhesive composition and an adherend material or is capable of forming a chemical bond, so as to obtain good adhesion to ceramic materials.

In the present invention, a silane compound represented by the above general formula [3] is used as the silane coupling agent which satisfies these conditions. Among the above functional groups of $R^6$, a (meth)acryloyl group, a vinyl group and a styryl group are connected to a polymer of a (meth)acrylate ester by copolymerization with a (meth)acrylate ester monomer. A mercapto group is connected to the polymer by formation of a chemical bond derived from a chain transfer/chain termination reaction. An epoxy group is connected to the polymer by formation of a chemical bond with a monomer having an amino group or carboxyl group capable of reacting with the epoxy group. In order to promote condensation of the silane coupling agent with a silanol group on the surface of the adherend, $R^7$, $R^8$ and $R^9$ each preferably represents a lower alkoxy group having 1 to 5 carbon atoms or a hydroxyl group. $R^7$ may be an alkyl group having 1 to 5 carbon atoms. Specific examples of the silane coupling agent which satisfies the above conditions include the following.

3-methacryloxypropylmethyldimethoxysilane

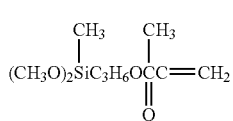
[Chemical Formula 6]

3-methacryloxypropyltrimethoxysilane

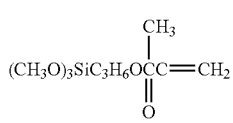
[Chemical Formula 7]

3-methacryloxypropylmethyldiethoxysilane

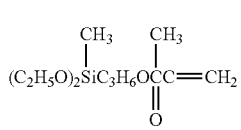
[Chemical Formula 8]

3-methacryloxypropyltriethoxysilane

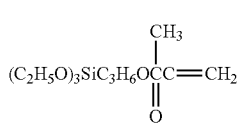
[Chemical Formula 9]

3-acryloxypropyltrimethoxysilane

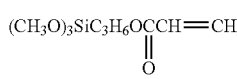
[Chemical Formula 10]

vinyltrimethoxysilane

[Chemical Formula 11]

vinyltriethoxysilane

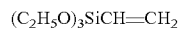
[Chemical Formula 12]

p-styryltrimethoxysilane

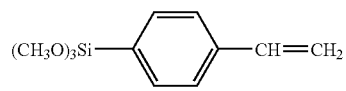
[Chemical Formula 13]

3-mercaptopropyltrimethoxysilane

[Chemical Formula 14]

3-mercaptopropylmethyldimethoxysilane

[Chemical Formula 15]

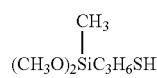

2-(3,4 epoxycyclohexyl)ethyltrimethoxysilane

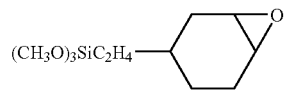
[Chemical Formula 16]

3-glycidoxypropyltrimethoxysilane

[Chemical Formula 17]

3-glycidoxypropylmethyldiethoxysilane

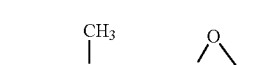
[Chemical Formula 18]

3-glycidoxypropyltriethoxysilane

[Chemical Formula 19]

The silane coupling agent as the component (a) is preferably a compound of the above general formula [3] in which $R^6$ has at least one functional group selected from the group consisting of a (meth)acryloyl group and a vinyl group; $R^7$ has a hydroxyl group, an alkyl group having 1 to 5 carbon atoms or an alkoxy group having 1 to 5 carbon atoms; and $R^8$ and $R^9$ each has a hydroxyl group or an alkoxy group having 1 to 5 carbon atoms.

The silane coupling agent as the component (a) is particularly preferably 3-methacryloxypropylmethyldimethoxysilane, 3-methacryloxypropyltrimethoxysilane, 3-methacryloxypropylmethyldiethoxysilane, 3-methacryloxypropyltriethoxysilane, or 3-acryloxypropyltrimethoxysilane.

The amount of the silane coupling agent as the component (a) may be appropriately selected according to the intended purposes of the composition, and is adjusted within a range from 1 to 60 parts by weight, and preferably from 5.0 to 50 parts by weight, based on the entire composition.

As the acidic group-containing polymerizable monomer as the component (b) in the present invention, all polymerizable monomers, which have been conventionally used as a dental acidic group-containing polymerizable monomer, can be used. Particularly, it is possible to select from a polymerizable monomer having a carboxyl group, a phosphate ester group, a phosphonic acid group, a pyrophosphoric acid group or a sulfonic acid group before use.

Examples of the monomer having a carboxyl group in the molecule, among the acidic group-containing polymerizable monomer as the component (b) in the present invention, include methacrylic acid, 4-(meth)acryloxyethyltrimellitic acid, 4-(meth)acryloyloxyethoxycarbonylphthalic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, maleic acid, acid anhydrides thereof, 5-(meth)acryloylaminopentylcarboxylic acid, 6-(meth)acryloyloxy-1,1-hexanedicarboxylic acid, 7-(meth)acryloyloxy-1,1-heptanedicarboxylic acid, 8-(meth)acryloyloxy-1,1-octanedicarboxylic acid, 10-(meth)acryloyloxy-1,1-decanedicarboxylic acid and 11-(meth)acryloyloxy-1,1-undecanedicarboxylic acid. The monomer further includes acid chlorides, alkali metal salts, alkali earth metal salts and ammonium salts thereof.

Examples of the monomer having a phosphate ester group, a phosphonic acid group or a pyrophosphoric acid group, among the acidic group-containing polymerizable monomer as the component (b) in the present invention, include 3-(meth)acryloxypropyl-3-phosphonopropionate, 3-(meth)acryloxypropyl-3-phosphonoacetate, 4-(meth)acryloxybutyl-3-phosphonopropionate, 4-(meth)acryloxybutylphosphonoacetate, 5-(meth)acryloxypentylphos-3-phonopropionate, 5-(meth)acryloxypentyl-3-phosphonoacetate, 6-(meth)acryloxyhexyl-3-phosphonopropionate, 6-(meth)acryloxyhexyl-3-phosphonoacetate, 10-(meth)acryloxydecyl-3-phosphonopropionate, 10-(meth)acryloxydecyl-3-phosphonoacetate, bis[2-(meth)acryloxyethyl]phosphate, 2-(meth)acryloyloxyethyldihydrogen phosphate, 3-(meth)acryloyloxypropyldihydrogen phosphate, 4-(meth)acryloyloxybutyldihydrogen phosphate, 5-(meth)acryloyloxypentyldihydrogen phosphate, 6-(meth)acryloyloxyhexyldihydrogen phosphate, 7-(meth)acryloyloxyheptyldihydrogen phosphate, 8-(meth)acryloyloxyoctyldihydrogen phosphate, 9-(meth)acryloyloxynonyldihydrogen phosphate, 10-(meth)acryloyloxydecyldihydrogen phosphate, 11-(meth)acryloyloxyundecyldihydrogen phosphate, 12-(meth)acryloyloxydodecyldihydrogen phosphate, 16-(meth)acryloyloxyhexadecyldihydrogen phosphate, 20-(meth)acryloyloxyeicosyldihydrogen phosphate, di[2-(meth)acryloyloxyethyl]hydrogen phosphate, di[4-(meth)acryloyloxybutyl]hydrogen phosphate, di[6-(meth)acryloyloxyhexyl]hydrogen phosphate, di[8-(meth)acryloyloxyoctyl]hydrogen phosphate, di[9-(meth)acryloyloxynonyl]hydrogen phosphate, di[10-(meth)acryloyloxydecyl]hydrogen phosphate, 1,3-di(meth)acryloyloxypropyl-2-dihydrogen phosphate, 2-(meth)acryloyloxyethylphenylhydrogen phosphate, 2-(meth)acryloyloxyethyl 2-bromoethylhydrogen phosphate, 2-(meth)acryloyloxyethylphenyl phosphonate, 10-(meth)acryloyloxydecylphosphonic acid, vinylphosphonic acid, p-vinylbenzylphosphonic acid; and polymerizable monomers described in Japanese Unexamined Patent Publication (Kokai) No. 62-281885, such as 2-methacryloyloxyethyl(4-methoxyphenyl)hydrogen phosphate, 2-methacryloyloxypropyl(4-methoxyphenyl)hydrogen phosphate, di[2-(meth)acryloyloxyethyl]pyrophosphate, di[4-(meth)acryloyloxybutyl]pyrophosphate, di[6-(meth)acryloyloxyhexyl]pyrophosphate, di[8-(meth)acryloyloxyoctyl]pyrophosphate and di[10-(meth)acryloyloxydecyl]pyrophosphate. The monomer further includes acid chlorides, alkali metal salts, alkali earth metal salts and ammonium salts thereof.

Examples of the monomer having a sulfonic acid group in the molecule, among the acidic group-containing polymerizable monomer as the component (b) in the present invention, include styrenesulfonic acid, 2-sulfoethyl (meth)acrylate, 6-sulfohexyl (meth)acrylate, 10-sulfodecyl (meth)acrylate and 2-(meth)acrylamide-2-methylpropanesulfonic acid. The monomer further includes acid chlorides, alkali metal salts, alkali earth metal salts and ammonium salts.

Among the acidic group-containing polymerizable monomer as the component (b) in the present invention, preferred polymerizable monomer is a (meth)acrylate-based monomer having a phosphonic acid group represented by the following general formula:

[Chemical Formula 20]

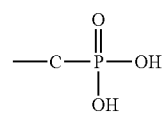

In the present invention, "(meth)acrylate" means acrylate or methacrylate.

Preferred is a phosphonic acid group-containing (meth)acrylate-based monomer represented by the following general formula [1]:

[Chemical Formula 21]

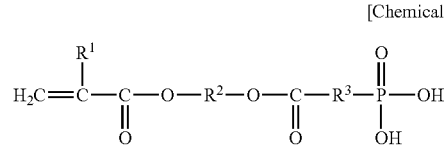

[1]

wherein $R^1$ represents a hydrogen atom or a methyl group; $R^2$ represents an optionally substituted an alkylene group having 1 to 20 carbon atoms, and $R^3$ represents an optionally substituted an alkylene group having 1 to 15 carbon atoms.

Examples of the alkylene group include those described as for the general formula [1]. The substituent which may be combined with $R^2$ or $R^3$ include, for example, an unsaturated group such as an alkenyl group or an alkynyl group, an alkyl group, or an alkyl group combined with a phenyl group.

Examples of the alkenyl group include:

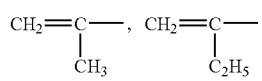
[Chemical Formula 22]

and examples of the alkyl group include —$CH_3$, —$C_2H_5$ and —$C_3H_7$, and examples of the alkyl group combined with a phenyl group include —$CH_2CH_2OC_6H_5$. Specific examples of the compound represented by the general formula [1] include the followings.

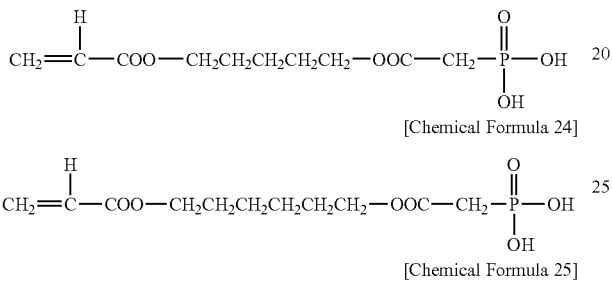
[Chemical Formula 23]

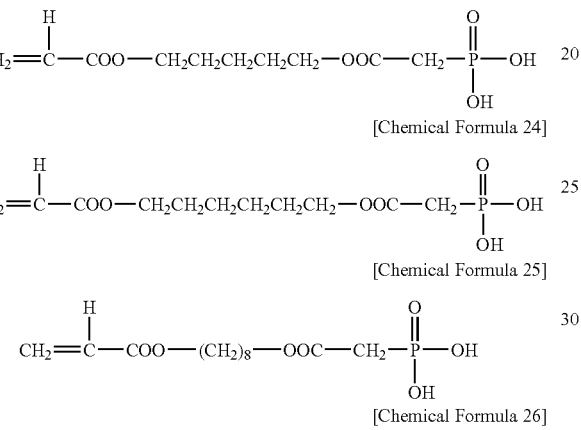
[Chemical Formula 24]

[Chemical Formula 25]

[Chemical Formula 26]

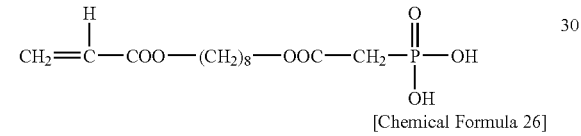
[Chemical Formula 27]

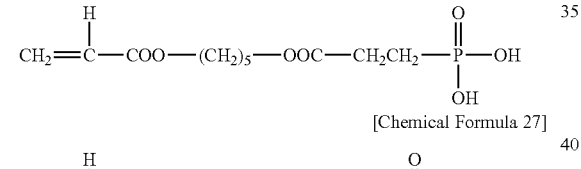
[Chemical Formula 28]

[Chemical Formula 29]

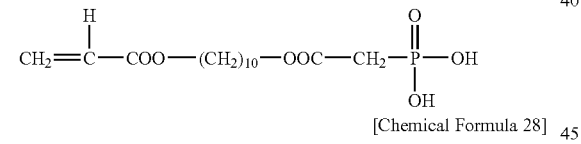
[Chemical Formula 30]

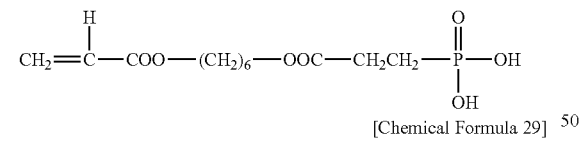
[Chemical Formula 31]

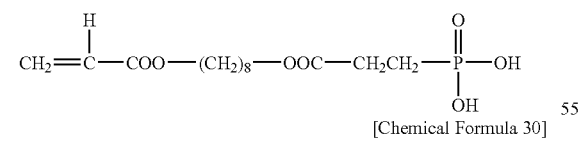

-continued

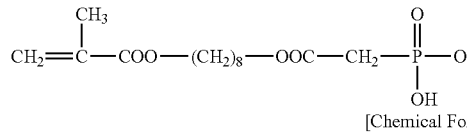
[Chemical Formula 32]

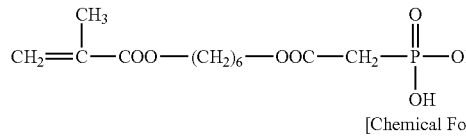
[Chemical Formula 33]

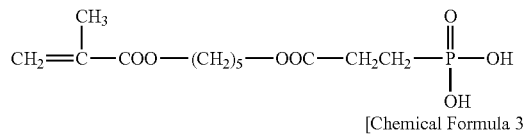
[Chemical Formula 34]

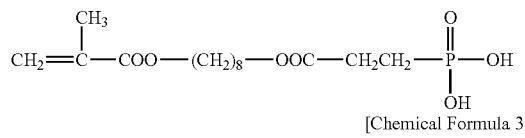
[Chemical Formula 35]

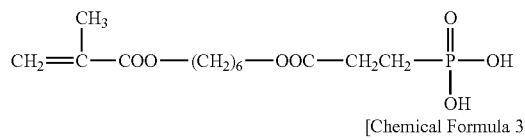
[Chemical Formula 36]

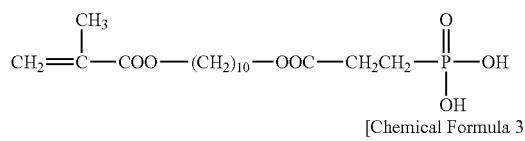
[Chemical Formula 37]

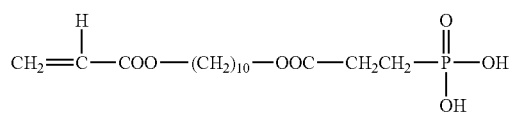
[Chemical Formula 38]

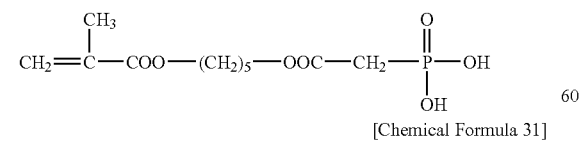

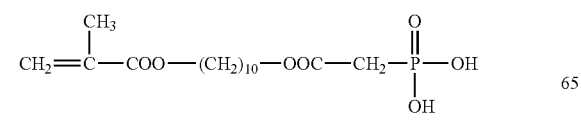

Particularly preferred phosphonic acid group-containing (meth)acrylate-based monomers are 6-methacryloxyhexyl-phosphonoacetate, 6-methacryloxyhexyl-3-phosphonopropionate, 10-methacryloxydecyl-3-phosphonopropionate or 10-methacryloxydecyl-phosphonoacetate, and particularly preferred phosphonic acid group-containing (meth)acrylate-based monomers are 6-methacryloxyhexyl-phosphonoacetate or 6-methacryloxyhexyl-3-phosphonopropionate.

The amount of the acidic group-containing polymerizable monomer as a component (b) may be appropriately selected according to the intended purposes of the composition, and is adjusted within a range from 1.0 to 20.0 parts by weight, and preferably from 4.0 to 15.5 parts by weight, based on 100 parts by weight of the silane coupling agent as the component (a).

The present invention has a volatile organic solvent as the component (c) is methanol, ethanol, isopropanol, butanol, acetone, ethyl acetate or isopropylether, or a radical polymerizable monomer such as (meth)acrylate ester, (meth)acrylamide or vinyl ester.

The volatile organic solvent is preferably ethanol or acetone, and the volatile organic solvent as the component (c) may be appropriately selected according to the intended purposes of the composition, and is adjusted within a range from 28 to 99 parts by weight, and preferably from 42.25 to 94.8 parts by weight.

As the sulfur group-containing polymerizable monomer in the present invention, all polymerizable monomers, which have conventionally been used as the dental sulfur group-containing polymerizable monomer, can be used.

Particularly preferred is a (meth)acrylate ester derivative having a disulfide cyclic group represented by the following general formula [2]:

[Chemical Formula 39]

$$H_2C=\underset{R^4}{C}-\underset{\underset{O}{\|}}{C}-O-R^5-O-\underset{\underset{O}{\|}}{C}-(CH_2)_n-CH\underset{S-S}{\overset{H_2C-CH_2}{<}}$$

[2]

wherein $R^4$ represents a hydrogen atom or a hydrocarbon group having 1 to 3 carbon atoms; $R^5$ represents an optionally substituted alkylene group having 1 to 30 carbon atoms; and n represents an integer of 0 to 15.

In the general formula [2], $R^4$ represents a hydrogen atom or a hydrocarbon group having 1 to 3 carbon atoms. Examples of the hydrocarbon group having 1 to 3 carbon atoms include —$CH_3$, —$C_2H_5$ and —$C_3H_7$. $R^4$ is preferably a hydrogen atom or a methyl group.

$R^5$ represents an optionally substituted alkylene group having 1 to 30 carbon atoms, preferably 1 to 14 carbon atoms, and more preferably 2 to 12 carbon atoms. Examples of the alkylene group include —$C_2H_4$—, —$C_3H_6$—, —$C_4H_8$— and —$C_{10}H_2O$—. The substituent, which may be combined with $R^5$, is an alkenyl group or an alkyl group, or an alkyl group combined with a phenyl group. Examples of the alkenyl group include:

[Chemical Formula 40]

$$CH_2=\underset{CH_3}{C}-,\quad CH_2=\underset{C_2H_5}{C}-$$

and examples of the alkyl group include —$CH_3$, —$C_2H_5$ and —$C_3H_7$, and examples of the alkyl group combined with a phenyl group include —$CH_2CH_2OC_6H_5$.

n represents an integer of 0 to 15. In the present invention, "(meth)acrylate" means acrylate or methacrylate.

Specific examples of the compound represented by the general formula [2] include the following compounds.

[Chemical Formula 41]

$CH_2=CHCOOCH_2CH_2OOC(CH_2)_4$—⟨disulfide cyclic⟩

$CH_2=CHCOOCH_2CHOOC(CH_2)_4$—⟨disulfide cyclic⟩
        |
        $CH_3$ $CH_2=CHCOOCH_2CHOOC(CH_2)_4$—⟨disulfide cyclic⟩
        |
        $CH_2CH_3$ $CH_2=CHCOOCH_2CHOOC(CH_2)_4$—⟨disulfide cyclic⟩
        |
        $CH_2CH_2OC_6H_5$ $CH_2=CHCOOCH_2CHOOC(CH_2)_4$—⟨disulfide cyclic⟩
        |
        $CH_2=CHCOOH_2C$

[Chemical Formula 42]

$CH_2=CHCOO(CH_2)_3OOC(CH_2)_4$—⟨disulfide cyclic⟩

$CH_2=CHCOO(CH_2)_4OOC(CH_2)_4$—⟨disulfide cyclic⟩

$CH_2=CHCOO(CH_2)_5OOC(CH_2)_4$—⟨disulfide cyclic⟩

$CH_2=CHCOO(CH_2)_6OOC(CH_2)_4$—⟨disulfide cyclic⟩

$CH_2=CHCOO(CH_2)_8OOC(CH_2)_4$—⟨disulfide cyclic⟩

[Chemical Formula 43]

$CH_2=CHCOO(CH_2)_{10}OOC(CH_2)_4$—⟨disulfide cyclic⟩

$CH_2=CHCOO(CH_2)_{12}OOC(CH_2)_4$—⟨disulfide cyclic⟩

$$CH_2=\underset{CH_3}{\overset{|}{C}}COOCH_2CH_2OOC(CH_2)_4\text{—⟨disulfide cyclic⟩}$$

$$CH_2=\underset{CH_3}{\overset{|}{C}}HCOOCH_2CHOOC(CH_2)_4\text{—⟨disulfide cyclic⟩}\\\quad\quad\quad\quad\quad\quad\quad\quad|\\\quad\quad\quad\quad\quad\quad\quad CH_3$$

$CH_2=CHCOOCH_2CHOOC(CH_2)_4$—⟨disulfide cyclic⟩ (with $CH_3$ on vinyl C and $CH_2CH_3$ on middle C)

[Chemical Formula 44]

$CH_2=CCOOCH_2CHOOC(CH_2)_4$—⟨disulfide cyclic⟩ (with $CH_3$ and $CH_2CH_2OC_8H_5$)

$CH_2=CCOOCH_2CHOOC(CH_2)_4$—⟨disulfide cyclic⟩
 |
 $CH_2=CCOOH_2C$
 |
 $CH_3$ $CH_2=CCOOCH_2CHOOC(CH_2)_4$—⟨disulfide cyclic⟩
 |
 $CH_2=CHCOOH_2C$
 |
 $CH_3$ $CH_2=CCOO(CH_2)_5OOC(CH_2)_4$—⟨disulfide cyclic⟩
 |
 $CH_3$ -continued

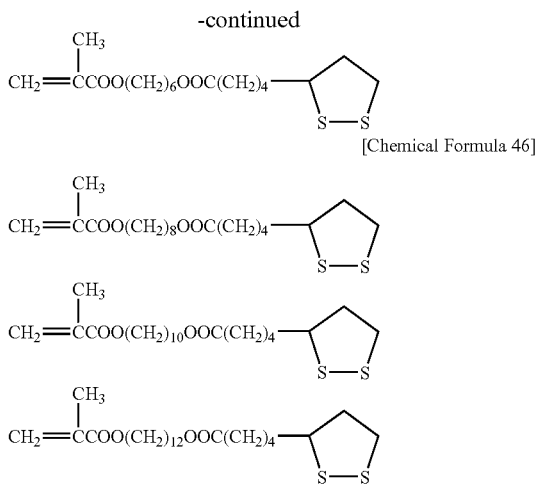

Particularly preferred compounds are 10-methacryloxydecyl-6,8-dithioctanate or 6-methacryloxyhexyl-6,8-dithioctanate.

The dental adhesive composition of the present invention contains the silane coupling agent as a component (a), the acidic group-containing polymerizable monomer as a component (b) and the volatile organic solvent as a component (c) as essential components, and other components can be appropriately selected and added. According to the applications, additive components such as radical polymerizable monomers, photopolymerization initiators, photopolymerization promoters, thermal polymerization initiators, polymerization catalysts, inorganic/organic fillers, polymerization inhibitors and pigment may be appropriately blended.

A radical polymerizable monomer as a component (e) can be added to the dental adhesive composition in the present invention. Specific examples of the radical polymerizable monomer as the component (e) include (meth)acrylates such as (meth)acrylic acid, methyl (meth)acrylate and ethyl (meth)acrylate, and alkyl side chain substituents with a hydroxyl group or halogen; urethane (meth)acrylates such as methoxydiethylene glycol (meth)acrylate, methoxypolyethylene glycol (meth)acrylate, ethylene glycol di(meth)acrylate, triethylene glycol di(meth)acrylate, tetraethylene glycol di(meth)acrylate, hexamethylene glycol di(meth)acrylate, polyethylene glycol di(meth)acrylate, propylene glycol di(meth)acrylate, polypropylene glycol di(meth)acrylate, neopentyl glycol di(meth)acrylate, 2,2'-bis{4-(meth)acryloxypropoxyphenyl}propane, 2,2'-bis{4-(meth)acryloxyethoxyphenyl}propane, 2,2'-bis{-4-(meth)acryloxydiethoxyphenyl}propane, bisphenol A di(meth)acrylate, bisphenol A diglycidyl (meth)acrylate, trimethylolpropane tri(meth)acrylate, trimethylolethane tri(meth)acrylate, tetramethylolethane tetra(meth)acrylate, epoxy-(meth)acrylate, and a reaction product of an organic diisocyanate and an alkyl (meth)acrylate; a polymerizable prepolymer having at least two polymerizable ethylenically unsaturated groups as a reaction product of a urethane prepolymer (a reaction product of an organic diisocyanate and diol) and a (meth)acrylate ester of an oxyalkanol having at least two carbon atoms; and a reaction product of a dibasic carboxylic acid having an ethylenically unsaturated group and a dihydric alcohol (namely, a polyester having an ethylenically unsaturated group).

These radical polymerizable monomers are used alone or in combination, and a combination of a bisphenol A diglycidyl (meth)acrylate of a polymerizable monomer, such as di(meth)acrylate, and triethylene glycol di(meth)acrylate is preferred.

As a polymerization initiator as a component (f) in the present invention, known compounds, which are usually used in the dental composition, are used without any limitation. The polymerization initiator is usually classified into a thermal polymerization initiator and a photopolymerization initiator.

As the photopolymerization initiator as the component (f), a photosensitizer, which generates a radical under light irradiation, can be used. Examples of the ultraviolet photosensitizer include benzoin-based compounds such as benzoin, benzoin methyl ether and benzoin ethyl ether; benzophenone-based compounds such as acetoinbenzophenone, p-chlorobenzophenone and p-methoxybenzophenone; and thioxanthone-based compounds such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone. Photosensitizers capable of initiating polymerization under irradiation with visible ray are preferably used since it does not required ultraviolet ray which is harmful to the human body. Examples thereof include α-diketones such as benzyl, camphorquinone, α-naphthyl, acetonaphthene, p,p'-dimethoxybenzyl, p,p'-dichlorobenzylacetyl, pentanedion, 1,2-phenanthrenequinone, 1,4-phenanthrenequinone, 3,4-phenanthrenequinone, 9,10-phenanthrenequinone and naphthoquinone. Preferably, camphorquinone is used.

It is also preferred to use the above photosensitizer in combination with a photopolymerization promoter. When tertiary amines are used as the photopolymerization promoter, a compound having an aromatic group substituted directly with a nitrogen atom is preferred. It is possible to use, as the photopolymerization promoter, tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N, N-dimethylaniline, m-chloro-N,N-dimethylaniline, p-dimethylaminobenzaldehyde, p-dimethylaminoacetophenone, p-dimethylaminobenzoic acid, ethyl p-dimethylaminobenzoate, amino p-dimethylaminobenzoate, N,N-dimethylanthralinic acid methyl ester, N,N-dihydroxyethylaniline, N,N-dihydroxyethyl-p-toluidine, p-dimethylaminophenyl alcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino)dimethanol; barbituric acids such as 5-butylbarbituric acid and 1-benzyl-5-phenylbarbituric acid, and metal salts thereof such as sodium salts and calcium salts; and tin compounds such as dibutyltin diacetate, dibutyltin dimaleate, dioctyltin dimaleate, dioctyltin dilaurate, dibutyltin dilaurate, dioctyltin diversatate, dioctyl-tin-S,S'-bis-isooctylmercapto acetate and tetramethyl-1,3-diacetoxydistanoxane. Among these photopolymerization promoters, at least one kind can be selected and used, and also two or more kinds can be used in combination. The amounts of the initiator and the promoter can be appropriately decided.

Furthermore, it is effective to add oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid and dimethylolpropionic acid, in addition to the tertiary amine, so as to improve photopolymerization promotion ability.

Specific examples of the thermal polymerization initiator, which is preferably used, include organic peroxides such as benzoyl peroxide, parachlorobenzoyl peroxide, 2,4-dichlorobenzoyl peroxide, acetyl peroxide, lauroyl peroxide, tertiary butyl peroxide, cumen hydroperoxide, 2,5-dimethylhexane-2,5-dihydro peroxide, methyl ethyl ketone peroxide and tertiary butyl peroxybenzoate; and azo compounds such as azobisisobutyronitrile, methyl azobisisobutyrate and azobiscyanovaleric acid.

Polymerization can be carried out at normal temperature by using the above organic peroxide in combination with an amine compound. As the amine compound, a secondary or tertiary amine in which an amine group is combined with an aryl group is preferably used in view of promotion of curing. For example, N,N-dimethyl-p-toluidine, N,N-dimethylaniline, N,N-β-hydroxyethyl-aniline, N,N-di(β-hydroxyethyl)-aniline, N,N-di(β-hydroxyethyl)-p-toluidine, N-methyl-aniline and N-methyl-p-toluidine are preferred.

It is preferred to further use a combination of the organic peroxide and the amine compound in combination with sulfinate or borate. Examples of the sulfinates include sodium benzenesulfinate, lithium benzenesulfinate and sodium p-toluenesulfinate. Examples of the borate include trialkylphenylboron, and sodium salts, lithium salts, potassium salts, magnesium salts, tetrabutylammonium salts and tetramethylammonium salts of trialkyl(p-fluorophenyl)boron (alkyl group is an n-butyl group, an n-octyl group, n-dodecyl group, etc.). Organoboron compounds, which react with oxygen or water to generate a radical, such as tributylborane and tributylborane partial oxide can also be used as an organic metal type polymerization initiator.

The dental adhesive composition of the present invention can be blended with various known additives as required. Examples of the additive include polymerization inhibitors, colorants, antitarnish agents, fluorescent agents, ultraviolet absorbers and antibacterial agents.

The component (g) of the present invention include an inorganic/organic filler. Examples of the inorganic/organic filler include organic polymer powders such as polymethyl methacrylate, polyethyl methacrylate, copolymer of methyl methacrylate and ethyl methacrylate, and polystyrene; organic fillers obtained by grinding a thermosetting resin cured article or a thermosetting resin cured article containing an inorganic filler; inorganic fillers (kaolin, talc, quartz, silica, colloidal silica, alumina, aluminosilicate, silicon nitride, barium sulfate, calcium phosphate, barium sulfate, glass powder) and composite fillers of inorganic fillers and organic fillers, which are suited for use of the composition in the form of powder/liquid, paste or slurry. Their surface may be coated with a coupling agent having a silanol group (γ-methacryloxypropyltrimethoxysilane, etc.).

Examples of the polymerization inhibitor include hydroquinone, hydroquinone monomethyl ether and butylated hydroxytoluene, and are suitable for stabilization of the shelf life of the composition.

EXAMPLES

The present invention will be described in detail by way of Examples and Comparative Examples. The present invention is not limited to the following Examples.

Abbreviations Shown in Examples (Chemical Name)

1) Silane Coupling Agent
   3-MPDES: 3-methacryloxypropylmethyldiethoxysilane
   3-MPTES: 3-methacryloxypropyltriethoxysilane 2) Acidic Group-Containing Polymerizable Monomer
   6-MHPA: 6-methacryloxyhexyl-phosphonoacetate
   6-MHPP: 6-methacryloxyhexyl-3-phosphonopropionate
   10-MDPP: 10-methacryloxydecyl-3-phosphonopropionate
   4-META: 4-methacryloxyethyltrimellitic anhydride
   PM: Phosmer M (manufactured by Uni-Chemical Co., Ltd.)

3) Radical Polymerizable Monomer
   Bis-GMA: Bisphenol A diglycidyl methacrylate
   3G: Triethylene glycol dimethacrylate 4) Photopolymerization Initiator, Photopolymerization promoter
   CQ: Camphorquinone
   DMBE: Ethyl p-dimethylaminobenzoate 5) Filler
   R-972: Fine silicic acid particles [manufactured by Nippon Aerosil Co. Ltd.]

6) Sulfur Atom-Containing Polymerizable Monomer
   10-MDDT: 10-methacryloxydecyl-6,8-dithioctanate Materials and Apparatuses Used in Test
   Resin cement: "RESICEM" [manufactured by SHOFU, INC.]
   Aluminum oxide plate: measuring about 15×15×2 mm [manufactured by JAPAN FINE CERAMICS CO., LTD.]
   Zirconium hydroxide plate: measuring about 15×15×2 mm [manufactured by JAPAN FINE CERAMICS CO., LTD.]
   Porcelain disk-shaped plate: measuring 15.0 in diameter× 5.0 mm [Porcelain for firing dental metal [manufactured by SHOFU, INC. under the trade name of "VINTAGE HALO"]
   Gold alloy plate: measuring 15×15×2 mm [manufactured by SHOFU, INC. under the trade name of "Super Gold Type 4"]
   Thermal cycle testing machine: manufactured by Tokyo Giken Inc.
   Instron's universal testing machine: manufactured by Instron Corp.

Test Nos. 1 to 21: Examples of Dental Primer or Dental Adhesive Material

A test regarding tensile adhesive strength was carried out on an example of a dental ceramic material of aluminum oxide or zirconium oxide using an aluminum oxide plate (measuring about 15×15×2 mm [manufactured by JAPAN FINE CERAMICS CO., LTD.]) and a zirconium oxide plate (measuring about 15×15×2 mm [manufactured by JAPAN FINE CERAMICS CO., LTD.]). An adhesive composition was prepared by mixing components in each weight ratio shown in Tables 1 to 4.

A flat surface of an aluminum oxide or zirconium oxide plate measuring about 15×15×2 mm was polished under running water using a silicone carbide paper #240 [manufactured by Sankyo-Rikagaku Co., Ltd.] and then polished using a silicone carbide paper #600 to obtain a smooth surface. The smooth surface was subjected to air abrasion (50 μm alumina beads, under a pressure of 2.5 kgf/cm$^2$), ultrasonic-cleaned and then air-dried to obtain an adherend.

An adhesive composition was applied on an adhesive surface of the adherend using a small brush and, after standing for 30 seconds, the adherend was dried using an air syringe until fluidity of the adhesive composition disappeared. Separately, an adhesive surface of a cylindrical stainless steel bar measuring 5 mm in diameter×10 mm in height was subjected to air abrasion (50 μm alumina beads, under a pressure of 5 kgf/cm$^2$), ultrasonic-cleaned and then air-dried to obtain a jig for measurement of an adhesive strength. "RESICEM" in the form of a uniform paste prepared by kneading was interposed between the adhesive surface of the adherend and the adhesive surface of the stainless steel bar, followed by bonding. Excess cement was removed by a small brush and a cement margin was photopolymerized for 10 seconds using "Shofu GRIP LIGHT II".

All seven specimens were immersed in water at 37° C. and immersed in water at 37° C. for 24 hours, and then a tensile adhesive strength was measured. In the measurement of the adhesive strength, the tensile adhesive strength was measured under conditions of a crosshead speed of 1 mm/min using a universal testing machine (manufactured by Instron Corp.). The entire adhesion test was carried out at room temperature of 23° C.±1° C.

An adhesive composition was prepared at each weight ratio shown in Tables 1 to 4, followed by mixing. The resultant adhesive composition was stored in a sealed state under a storage environment at 23° C. within 24 hours. The measured tensile adhesive strength was taken as an "initial" tensile adhesive strength. Separately, an adhesive composition was prepared at each weight ratio shown in Tables 1 to 4, followed by mixing. The resultant adhesive composition was stored in a sealed state under a storage environment at 50° C. for 2 months. The measured tensile adhesive strength was taken as a tensile adhesive strength "after storage at 50° C. for 2 months".

Using porcelain for firing dental metal [manufactured by SHOFU, INC. under the trade name of "VINTAGE HALO"] as a dental ceramic material containing a silicon dioxide as a main component, a disk-shaped (measuring 15.0 in diameter×5.0 mm) fired material was made using a vacuum electric furnace for firing porcelain [manufactured by SHOFU, INC. under the trade name of "TWIN MAT"] and a test on a tensile adhesive strength was carried out. An adhesive composition was prepared by mixing components in each weight ratio shown in Tables 1 to 4.

A flat surface of the disk-shaped (measuring 15.0 in diameter×5.0 mm) fired material was polished under running water using a silicone carbide paper #240 [manufactured by Sankyo-Rikagaku Co., Ltd.] and then polished using a silicone carbide paper #600 to obtain a smooth surface. The smooth surface was subjected to air abrasion (50 μm alumina beads, under a pressure of 2.5 kgf/cm$^2$), ultrasonic-cleaned and then air-dried to obtain an adherend.

An adhesive composition was applied on an adhesive surface of the adherend using a small brush and, after standing for 30 seconds, the adherend was dried using an air syringe until fluidity of the adhesive composition disappeared. Separately, an adhesive surface of a cylindrical stainless COBALTAM (cobalt-chromium alloy: manufactured by SHOFU, INC.) bar measuring 5 mm in diameter×10 mm in height was subjected to air abrasion (50 μm alumina beads, under a pressure of 5 kgf/cm$^2$), ultrasonic-cleaned and then air-dried to obtain a jig for measurement of an adhesive strength. "RESICEM" in the form of a uniform paste prepared by kneading was interposed between the adhesive surface of the adherend and the adhesive surface of the stainless steel bar, followed by bonding. Excess cement was removed by a small brush and a cement margin was photopolymerized for 10 seconds using "Shofu GRIP LIGHT II".

All seven specimens were immersed in water at 37° C. and immersed in water at 37° C. for 24 hours, and then a tensile adhesive strength was measured. In the measurement of the adhesive strength, the tensile adhesive strength was measured under conditions of a crosshead speed of 1 mm/min using a universal testing machine (manufactured by Instron Corp.). The entire adhesion test was carried out at room temperature of 23° C.±1° C.

An adhesive composition was prepared at each weight ratio shown in Tables 1 to 4, followed by mixing. The resultant adhesive composition was stored in a sealed state under a storage environment at 23° C. within 24 hours. The measured tensile adhesive strength was taken as an "initial" tensile adhesive strength. Separately, an adhesive composition was prepared at each weight ratio shown in Tables 1 to 4, followed by mixing. The resultant adhesive composition was stored in a sealed state under a storage environment at 50° C. for 2 months. The measured tensile adhesive strength was taken as a tensile adhesive strength "after storage at 50° C. for 2 months".

Using a gold alloy plate (measuring about 15×15×2 mm [Super Gold Type 4 (alloy)) as an example of a dental noble metal material, a test on a tensile adhesive strength was carried out. An adhesive composition was prepared by mixing components in each weight ratio shown in Tables 1 to 4.

A flat surface of an aluminum oxide or zirconium oxide plate measuring about 15×15×2 mm was polished under running water using a silicone carbide paper #600 [manufactured by Sankyo-Rikagaku Co., Ltd.] to obtain a smooth surface. The smooth surface was subjected to air abrasion (50 μm alumina beads, under a pressure of 2.5 kgf/cm$^2$), ultrasonic-cleaned and then air-dried to obtain an adherend.

An adhesive composition was applied on an adhesive surface of the adherend using a small brush and, after standing for 30 seconds, the adherend was dried using an air syringe until fluidity of the adhesive composition disappeared. Separately, an adhesive surface of a cylindrical stainless steel bar measuring 5 mm in diameter×10 mm in height was subjected to air abrasion (50 μm alumina beads, under a pressure of 5 kgf/cm$^2$), ultrasonic-cleaned and then air-dried to obtain a jig for measurement of an adhesive strength. "RESICEM" in the form of a uniform paste prepared by kneading was interposed between the adhesive surface of the adherend and the adhesive surface of the stainless steel bar, followed by bonding. Excess cement was removed by a small brush and a cement margin was photopolymerized for 10 seconds using "Shofu GRIP LIGHT II".

All seven specimens were immersed in water at 37° C. and immersed in water at 37° C. for 24 hours, and then a tensile adhesive strength was measured. In the measurement of the adhesive strength, the tensile adhesive strength was measured under conditions of a crosshead speed of 1 mm/min using a universal testing machine (manufactured by Instron Corp.). The entire adhesion test was carried out at room temperature of 23° C.±1° C.

An adhesive composition was prepared at each weight ratio shown in Tables 1 to 4, followed by mixing. The resultant adhesive composition was stored in a sealed state under a storage environment at 23° C. within 24 hours. The measured tensile adhesive strength was taken as an "initial" tensile adhesive strength. Separately, an adhesive composition was prepared at each weight ratio shown in Tables 1 to 4, followed by mixing. The resultant adhesive composition was stored in a sealed state under a storage environment at 50° C. for 2 months. The measured tensile adhesive strength was taken as a tensile adhesive strength "after storage at 50° C. for 2 months".

Test Nos. 22 to 23: Examples of Dental Primer or Dental Adhesive Material

Using an aluminum oxide plate (measuring about 15×15×2 mm [manufactured by JAPAN FINE CERAMICS CO., LTD.]) and a zirconium oxide plate (measuring about 15×15×2 mm [manufactured by JAPAN FINE CERAMICS CO., LTD.]) as examples of a dental ceramic material of aluminum oxide or zirconium oxide, a test on a shear adhesive strength was carried out. An adhesive composition was prepared by mixing components in each weight ratio shown in Table 5.

A flat surface of an aluminum oxide or zirconium oxide plate measuring about 15×15×2 mm was polished under running water using a silicone carbide paper #240 [manufactured by Sankyo-Rikagaku Co., Ltd.] and then polished using a silicone carbide paper #600 to obtain a smooth surface. The smooth surface was subjected to air abrasion (50 μm alumina beads, under a pressure of 2.5 kgf/cm$^2$), ultrasonic-cleaned and then air-dried to obtain an adherend. A double-stick tape with holes having a diameter of 4 mm was applied on the polished adhesive surface thereby defining the adhesive surface.

An adhesive composition was applied on an adhesive surface of the adherend using a small brush and, after standing for 30 seconds, the adherend was dried using an air syringe until fluidity of the adhesive composition disappeared. Subsequently, the adherend was irradiated with light using Shofu GRIP LIGHT II [manufactured by SHOFU, INC.] for 10 seconds. After fixing a plastic mold measuring 4 mm in diameter and 2 mm in height to an adhesion defined surface frame, a photopolymerizable composite resin "Beautiful" [manufactured by SHOFU, INC.] was filled in the mold. After shielding the air with a cover glass, a composite resin was cured by irradiating with light for 30 seconds using Shofu GRIP LIGHT II and the mold was removed to make an adhesion test specimen.

All seven specimens were immersed in water at 37° C. and immersed in water at 37° C. for 24 hours, and then a shear adhesive strength was measured. In the measurement of the adhesive strength, the shear adhesive strength was measured under conditions of a crosshead speed of 1 mm/min using a universal testing machine (manufactured by Instron Corp.). The entire adhesion test was carried out at room temperature of 23° C.±1° C.

An adhesive composition was prepared at each weight ratio shown in Table 5, followed by mixing. The resultant adhesive composition was stored in a sealed state under a storage environment at 23° C. within 24 hours. The measured shear adhesive strength was taken as an "initial" shear adhesive strength. Separately, an adhesive composition was prepared at each weight ratio shown in Table 5, followed by mixing. The resultant adhesive composition was stored in a sealed state under a storage environment at 50° C. for 2 months. The measured shear adhesive strength was taken as a shear adhesive strength "after storage at 50° C. for 2 months".

Using porcelain for firing dental metal [manufactured by SHOFU, INC. under the trade name of "VINTAGE HALO"] as a dental ceramic material containing a silicon dioxide as a main component, a disk-shaped (measuring 15.0 in diameter×5.0 mm) fired material was made using a vacuum electric furnace for firing porcelain [manufactured by SHOFU, INC. under the trade name of "TWIN MAT"] and a test on a shear adhesive strength was carried out. An adhesive composition was prepared by mixing components in each weight ratio shown in Tables 1 to 4.

A flat surface of the disk-shaped (measuring 15.0 in diameter×5.0 mm) fired material was polished under running water using a silicone carbide paper #240 [manufactured by Sankyo-Rikagaku Co., Ltd.] and then polished using a silicone carbide paper #600 to obtain a smooth surface. The smooth surface was ultrasonic-cleaned and then air-dried to obtain an adherend.

An adhesive composition was applied on an adhesive surface of the adherend using a small brush and, after standing for 30 seconds, the adherend was dried using an air syringe until fluidity of the adhesive composition disappeared. Subsequently, the adherend was irradiated with light using Shofu GRIP LIGHT II [manufactured by SHOFU, INC.] for 10 seconds. After fixing a plastic mold measuring 4 mm in diameter and 2 mm in height to an adhesion defined surface frame, a photopolymerizable composite resin "Beautifil" [manufactured by SHOFU, INC.] was filled in the mold. After shielding the air with a cover glass, a composite resin was cured by irradiating with light for 30 seconds using Shofu GRIP LIGHT II and the mold was removed to make an adhesion test specimen.

All seven specimens were immersed in water at 37° C. and immersed in water at 37° C. for 24 hours, and then a shear adhesive strength was measured. In the measurement of the adhesive strength, the shear adhesive strength was measured under conditions of a crosshead speed of 1 mm/min using a universal testing machine (manufactured by Instron Corp.). The entire adhesion test was carried out at room temperature of 23° C.±1° C.

An adhesive composition was prepared at each weight ratio shown in Table 5, followed by mixing. The resultant adhesive composition was stored in a sealed state under a storage environment at 23° C. within 24 hours. The measured shear adhesive strength was taken as an "initial" shear adhesive strength. Separately, an adhesive composition was prepared at each weight ratio shown in Table 5, followed by mixing. The resultant adhesive composition was stored in a sealed state under a storage environment at 50° C. for 2 months. The measured shear adhesive strength was taken as a shear adhesive strength "after storage at 50° C. for 2 months".

Using a gold alloy plate (measuring about 15×15×2 mm [Super Gold Type 4, manufactured by SHOFU, INC.] as an example of a dental noble metal material, a test on a shear adhesive strength was carried out. An adhesive composition was prepared by mixing components in each weight ratio shown in Table 5.

A flat surface of a gold alloy plate measuring 15×15×2 mm was polished under running water using a silicone carbide paper #600 [manufactured by Sankyo-Rikagaku Co., Ltd.] to obtain a smooth surface. The smooth surface was ultrasonic-cleaned and then air-dried to obtain an adherend. A double-stick tape with holes having a diameter of 4 mm was applied on the polished adhesive surface thereby defining the adhesive surface.

An adhesive composition was applied on an adhesive surface of the adherend using a small brush and, after standing for 30 seconds, the adherend was dried using an air syringe until fluidity of the adhesive composition disappeared. Subsequently, the adherend was irradiated with light using Shofu GRIP LIGHT II [manufactured by SHOFU, INC.] for 10 seconds. After fixing a plastic mold measuring 4 mm in diameter and 2 mm in height to an adhesion defined surface frame, a photopolymerizable composite resin "Beautiful" [manufactured by SHOFU, INC.] was filled in the mold. After shielding the air with a cover glass, a composite resin was cured by irradiating with light for 30 seconds using Shofu GRIP LIGHT II and the mold was removed to make an adhesion test specimen.

All seven specimens were immersed in water at 37° C. and immersed in water at 37° C. for 24 hours, and then a shear adhesive strength was measured. In the measurement of the adhesive strength, the shear adhesive strength was measured under conditions of a crosshead speed of 1 mm/min using a universal testing machine (manufactured by Instron Corp.). The entire adhesion test was carried out at room temperature of 23° C.±1° C.

An adhesive composition was prepared at each weight ratio shown in Table 5, followed by mixing. The resultant adhesive composition was stored in a sealed state under a storage environment at 23° C. within 24 hours. The measured shear adhesive strength was taken as an "initial" shear adhesive strength. Separately, an adhesive composition was prepared at each weight ratio shown in Table 5, followed by mixing. The resultant adhesive composition was stored in a sealed state under a storage environment at 50° C. for 2 months. The measured tensile adhesive strength was taken as a shear adhesive strength "after storage at 50° C. for 2 months".

TABLE 1

| | | | Test No. | | | | | | | |
|---|---|---|---|---|---|---|---|---|---|---|
| | | | 1 | 2 | 3 | 4 | 5 | 6 | 7 | 8 |
| | | | Examples and Comparative Examples | | | | | | | |
| | | | Example 1 | Example 2 | Example 3 | Example 4 | Example 5 | Example 6 | Example 7 | Example 8 |
| Amounts [parts by weight] and names of components (a), (b), (c) and (d) | (a) Silane coupling agent | 3MPTES | 40.0 | 40.0 | 40.0 | 4.00 | 4.00 | 20.00 | 50.00 | 60.00 |
| | (b) Acidic group-containing polymerizable monomer | 6-MHPA | 0.64 | 2.48 | 7.44 | 0.25 | 0.06 | 1.24 | 6.20 | 3.72 |
| | (c) Volatile organic solvent | Acetone | 29.18 | 28.26 | 52.06 | 47.45 | 95.44 | 78.26 | 21.40 | |
| | | Ethanol | 29.68 | 28.76 | | 47.80 | | | 21.90 | 35.78 |
| | (d) Sulfur atom-containing polymerizable monomer | 10-MDDT | 0.50 | 0.50 | 0.50 | 0.50 | 0.50 | 0.50 | 0.50 | 0.50 |
| Total amount of components (a), (b), (c) and (d) [parts by weight] | | | 100.0 | 100.0 | 100.0 | 100.0 | 100.0 | 100.0 | 100.0 | 100.0 |
| Amount of component (b) based on 100 parts by weight of component (a) [parts by weight] | | | 1.6 | 6.2 | 18.6 | 6.2 | 1.6 | 6.2 | 12.4 | 6.2 |
| Tensile adhesive strength [MPa] | Porcelain | Initial | 20.8 | 26.9 | 29.2 | 22.1 | 18.8 | 26.4 | 24.6 | 30.8 |
| | | After storage at 50° C. for 2 months | 19.5 | 25.0 | 22.1 | 17.1 | 18.1 | 20.7 | 21.5 | 30.6 |
| | Alumina | Initial | 25.2 | 23.9 | 21.7 | 23.1 | 19.7 | 19.7 | 22.8 | 23.3 |
| | | After storage at 50° C. for 2 months | 21.4 | 22.9 | 25.3 | 22.7 | 21.6 | 22.9 | 23.7 | 26.6 |
| | Zirconia | Initial | 16.0 | 21.9 | 24.5 | 20.9 | 21.7 | 21.2 | 18.0 | 18.4 |
| | | After storage at 50° C. for 2 months | 23.9 | 21.4 | 20.8 | 24.4 | 19.3 | 18.9 | 19.4 | 23.4 |
| | Gold alloy | Initial | 24.5 | 25.4 | 26.8 | 21.7 | 26.6 | 24.0 | 22.2 | 23.8 |
| | | After storage at 50° C. for 2 months | 23.1 | 26.9 | 27.6 | 24.6 | 23.4 | 22.5 | 23.5 | 21.8 |

TABLE 2

| | | | Test No. | | | |
|---|---|---|---|---|---|---|
| | | | 9 | 10 | 11 | 12 |
| | | | Examples and Comparative Examples | | | |
| | | | Comparative Example 1 | Comparative Example 2 | Comparative Example 3 | Comparative Example 4 |
| Amounts [parts by weight] and names of components (a), (b), (c) and (d) | (a) Silane coupling agent | 3MPTES | 20.0 | 20.0 | 20.0 | 20.0 |
| | (b) Acidic group-containing polymerizable monomer | 6-MHPA | | 1.2 | 5.0 | 0.1 |
| | (c) Volatile organic solvent | Acetone | | | | |
| | | Ethanol | 79.5 | 78.8 | 74.5 | 79.4 |
| | (d) Sulfur atom-containing polymerizable monomer | 10-MDDT | 0.5 | | 0.5 | 0.5 |
| Total amount of components (a), (b), (c) and (d) [parts by weight] | | | 100.0 | 100.0 | 100.0 | 100.0 |
| Amount of component (b) based on 100 parts by weight of component (a) [parts by weight] | | | 0.0 | 6.2 | 25.0 | 0.5 |

TABLE 2-continued

|  |  |  | Test No. | | | |
| --- | --- | --- | --- | --- | --- | --- |
|  |  |  | 9 | 10 | 11 | 12 |
|  |  |  | Examples and Comparative Examples | | | |
|  |  |  | Comparative Example 1 | Comparative Example 2 | Comparative Example 3 | Comparative Example 4 |
| Tensile adhesive strength [MPa] | Porcelain | Initial | 9.1 | 22.0 | 20.4 |  |
|  |  | After storage at 50° C. for 2 months | 8.8 | 21.0 | 9.7 | 8.9 |
|  | Alumina | Initial | 10.2 | 19.8 | 20.4 | 8.0 |
|  |  | After storage at 50° C. for 2 months | 8.9 | 19.8 | 20.3 | 7.9 |
|  | Zirconia | Initial | 6.5 | 16.5 | 17.7 | 7.6 |
|  |  | After storage at 50° C. for 2 months | 6.6 | 16.5 | 16.2 | 6.2 |
|  | Gold alloy | Initial | 11.6 | 9.7 | 15.6 | 10.2 |
|  |  | After storage at 50° C. for 2 months | 11.0 | 8.1 | 16.6 | 10.6 |

TABLE 3

|  |  |  | Test No. | | | | | |
| --- | --- | --- | --- | --- | --- | --- | --- | --- |
|  |  |  | 13 | 14 | 15 | 16 | 17 | 18 |
|  |  |  | Examples and Comparative Examples | | | | | |
|  |  |  | Comparative Example 5 | Comparative Example 6 | Example 9 | Example 10 | Example 11 | Comparative Example 7 |
| Amounts [parts by weight] and names of components (a), (b), (c) and (d) | (a) Silane coupling agent | 3MPTES | 20.0 | 20.0 | 20.0 | 20.0 | 20.0 | 20.0 |
|  | (b) Acidic group-containing polymerizable monomer | PM |  | 0.05 | 0.6 | 1.2 | 2.4 | 5.00 |
|  | (c) Volatile organic solvent | Acetone |  |  |  |  |  |  |
|  |  | Ethanol | 79.5 | 79.5 | 78.9 | 78.3 | 77.1 | 74.5 |
|  | (d) Sulfur atom-containing polymerizable monomer | 10-MDDT | 0.5 | 0.50 | 0.5 | 0.5 | 0.5 | 0.50 |
| Total amount of components (a), (b), (c) and (d) [parts by weight] |  |  | 100.0 | 100.0 | 99.5 | 100.0 | 100.0 | 100.0 |
| Amount of component (b) based on 100 parts by weight of component (a) [parts by weight] |  |  | 0.0 | 0.3 | 3.0 | 6.0 | 12.0 | 25.0 |
| Tensile adhesive strength [MPa] | Porcelain | Initial | 4.7 | 4.9 | 21.7 | 16.0 | 17.6 | 16.9 |
|  |  | After storage at 50° C. for 2 months | 3.9 | 5.7 | 16.6 | 15.4 | 16.9 | 5.7 |
|  | Alumina | Initial | 8.3 | 7.7 | 24.1 | 23.7 | 23.1 | 20.3 |
|  |  | After storage at 50° C. for 2 months | 8.2 | 6.8 | 19.4 | 20.8 | 19.2 | 13.6 |
|  | Zirconia | Initial | 7.1 | 6.9 | 20.8 | 19.4 | 22.4 | 22.5 |
|  |  | After storage at 50° C. for 2 months | 6.0 | 5.6 | 13.7 | 20.3 | 20.1 | 17.6 |
|  | Gold alloy | Initial | 9.7 | 10.2 | 15.5 | 16.9 | 18.6 | 16.3 |
|  |  | After storage at 50° C. for 2 months | 10.1 | 11.2 | 15.7 | 17.6 | 15.9 | 13.7 |

TABLE 4

|  |  |  | Test No. 19 | Test No. 20 | Test No. 21 |
|---|---|---|---|---|---|
|  |  |  | Examples and Comparative Examples | | |
|  |  |  | Example 12 | Example 13 | Example 14 |
| Amounts [parts by weight] and names of components (a), (b), (c) and (d) | (a) Silane coupling agent | 3MPTES | 40.00 | 40.00 | 40.00 |
|  | (b) Acidic group-containing polymerizable monomer | 6-MHPP | 3.72 | | |
|  |  | 10-MDPP | | 3.72 | |
|  |  | 4-META | | | 3.72 |
|  | (c) Volatile organic solvent | Acetone | 7.98 | 55.78 | 18.26 |
|  |  | Ethanol | 47.80 | | 37.52 |
|  | (d) Sulfur atom-containing polymerizable monomer | 10-MDDT | 0.50 | 0.50 | 0.50 |
| Total amount of components (a), (b), (c) and (d) [parts by weight] | | | 100.0 | 100.0 | 100.0 |
| Amount of component (b) based on 100 parts by weight of component (a) [parts by weight] | | | 9.3 | 9.3 | 9.3 |
| Tensile adhesive strength [MPa] | Porcelain | Initial | 24.9 | 25.6 | 26.0 |
|  |  | After storage at 50° C. for 2 months | 21.9 | 22.2 | 20.6 |
|  | Alumina | Initial | 23.9 | 22.8 | 24.9 |
|  |  | After storage at 50° C. for 2 months | 24.4 | 23.0 | 24.3 |
|  | Zirconia | Initial | 22.2 | 17.1 | 19.0 |
|  |  | After storage at 50° C. for 2 months | 17.5 | 17.8 | 19.5 |
|  | Gold alloy | Initial | 25.7 | 25.8 | 24.9 |
|  |  | After storage at 50° C. for 2 months | 24.3 | 23.9 | 23.8 |

TABLE 5

|  |  |  | Test No. 22 | Test No. 23 |
|---|---|---|---|---|
|  |  |  | Examples and Comparative Examples | |
|  |  |  | Example 15 | Example 16 |
| Amounts [parts by weight] and names of components (a), (b), (c) and (d) | (a) Silane coupling agent | 3MPTES | 33.17 | 28.60 |
|  | (b) Acidic group-containing polymerizable monomer | 6-MHPA | 2.06 | 2.10 |
|  | (c) Volatile organic solvent | Ethanol | 47.18 | 16.80 |
|  | (d) Sulfur atom-containing polymerizable monomer | 10-MDDT | 0.50 | 0.50 |
| Radical polymerizable initiator | | Bis-GMA | 11.61 | 32.00 |
|  | | 3G | 4.98 | 14.50 |
| Photopolymerization initiator | | CQ | 0.25 | 0.25 |
| Photopolymerization promoter | | DMBE | 0.25 | 0.25 |
| Filler | | R-972 | 0.00 | 5.00 |
| Total amount of components [parts by weight] | | | 100.00 | 100.00 |
| Amount of component (b) based on 100 parts by weight of component (a) [parts by weight] | | | 6.2 | 7.3 |
| Shear adhesive strength [MPa] | Porcelain | Initial | 20.7 | 18.6 |
|  |  | After storage at 50° C. for 2 months | 18.5 | 19.2 |
|  | Alumina | Initial | 17.0 | 16.5 |
|  |  | After storage at 50° C. for 2 months | 18.8 | 15.4 |
|  | Zirconia | Initial | 19.4 | 18.5 |
|  |  | After storage at 50° C. for 2 months | 18.7 | 17.9 |

TABLE 5-continued

| | | Test No. | |
| --- | --- | --- | --- |
| | | 22 | 23 |
| | | Examples and Comparative Examples | |
| | | Example 15 | Example 16 |
| Gold alloy | Initial | 25.5 | 24.3 |
| | After storage at 50° C. for 2 months | 22.8 | 26.2 |

What is claimed is:

1. A one-pack type dental primer composition comprising:
a silane coupling agent as a component (a),
a phosphonic acid group-containing (meth)acrylate-based monomer represented by the following formula (1):

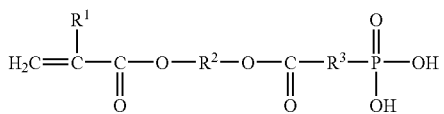

[1]

wherein $R^1$ represents a hydrogen atom or a methyl group, $R^2$ represents an optionally substituted an alkylene group having 1 to 20 carbon atoms, and $R^3$ represents an optionally substituted an alkylene group having 1 to 15 carbon atoms as a component (b),
a volatile organic solvent as a component (c), and
a (meth)acrylate ester derivative having a disulfide cyclic group represented by the following formula (2):

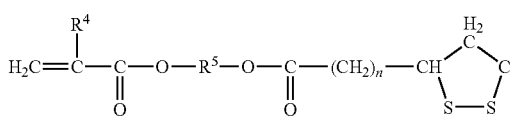

[2]

wherein $R^4$ represents a hydrogen atom or a hydrocarbon group having 1 to 3 carbon atoms, $R^5$ represents an optionally substituted alkylene group having 1 to 30 carbon atoms, and n represents an integer of 0 to 15 as a component (d),
wherein the content of the component (a) is from 1 to 60 parts by weight based on the entire composition and the content of the component (b) is from 1.0 to 20.0 parts by weight based on 100 parts by weight of the component (a).

2. A one-pack type dental primer composition comprising:
a silane coupling agent as a component (a),
a phosphonic acid group-containing (meth)acrylate-based monomer represented by the following formula (1):

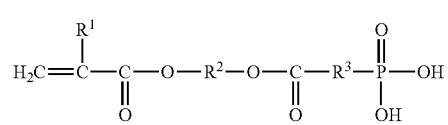

[1]

wherein $R^1$ represents a hydrogen atom or a methyl group, $R^2$ represents an optionally substituted alkylene group having 1 to 20 carbon atoms, and $R^3$ represents an optionally substituted alkylene group having 1 to 15 carbon atoms as a component (b),
a (meth)acrylate ester derivative having a disulfide cyclic group represented by the following formula (2):

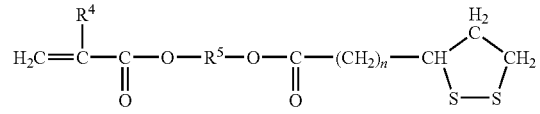

[2]

wherein $R^4$ represents a hydrogen atom or a hydrocarbon group having 1 to 3 carbon atoms, $R^5$ represents an optionally substituted alkylene group having 1 to 30 carbon atoms, and n represents an integer of 0 to 15 as a component (d),
a radical polymerizable monomer as a component (e), and
a photopolymerization initiator as a component (f),
wherein the content of the component (b) is from 1.0 to 20.0 parts by weight based on 100 parts by weight of the component (a).

* * * * *